United States Patent [19]

Gradeff et al.

[11] Patent Number: 4,801,692
[45] Date of Patent: Jan. 31, 1989

[54] CERIC ALKANOLATOAMINES

[75] Inventors: Peter S. Gradeff, Pottersville; Fred G. Schreiber, Highland Park, both of N.J.

[73] Assignee: Rhone-Poulenc Inc., N.J.

[21] Appl. No.: 895,560

[22] Filed: Aug. 11, 1986

[51] Int. Cl.[4] .................................................. C07F 5/00
[52] U.S. Cl. ........................................ 534/15; 501/152; 502/65; 502/102; 502/150; 106/316
[58] Field of Search ............................................ 534/15

[56] References Cited

U.S. PATENT DOCUMENTS

| 4,489,000 | 12/1984 | Gradeff et al. | 534/15 |
| 4,492,655 | 1/1985 | Gradeff et al. | 534/15 |
| 4,599,201 | 7/1986 | Gradeff et al. | 534/15 X |
| 4,647,401 | 3/1987 | Gradeff et al. | 534/15 X |
| 4,663,439 | 5/1987 | Gradeff et al. | 534/15 |

OTHER PUBLICATIONS

Batwara, et al, Alkoxides of Gadolinium, Erbium, and Ytterbium. "Chemistry and Industry", Aug. 6, 1966, pp. 1370, 1379.
Kadantseva, et al, Cerium Chloride-Triethanolamine Hydrochloride-Water System, Khim, Khim, "Tekhaol", 20(5), 787, Jan. 21, 1986.
Bradley et al., *J. Chem. Soc.*, pp. 2260–2264 (1956).
Bradley et al., *Metal Alkoxides*, Academic Press, 1978, pp. 226–241.
Golub et al. *Zh. Neorg. Khim.*, 14(3), 720–722 (1969).
CA 87(12): 91463p, "Cerium Chloride-Triethanolamine Hydrochloride-Water System".

*Primary Examiner*—John F. Terapane
*Assistant Examiner*—Virginia B. Caress
*Attorney, Agent, or Firm*—Morgan & Finnegan

[57] ABSTRACT

A compound having the formula

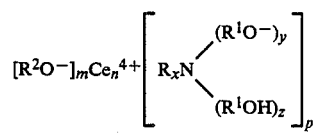

wherein R is one or more moieties selected from the group consisting of hydrogen and alkyl having from 1 to 20 carbon atoms, $R^2$ is an alkyl group having from 1 to 20 carbon atoms, $R^1$ is an alkyl group having from 1 to 20 carbon atoms, m is an integer from 0 to 3, y is an integer from 1 to 3, x and z are each an integer from 0 to 2, n and p are each an integer from 1 to 20, with the proviso that $m+yp=4n$, the sum of x, y and z is 3.

28 Claims, No Drawings

CERIC ALKANOLATOAMINES

BACKGROUND OF THE INVENTION

The rare earth or lanthanide metals comprise some 15 elements. Among them, cerium is of particular interest for several reasons. Cerium is the most abundant rare earth metal, representing about 47% of all of the rare earth metals found in the earth. It is three times more abundant than metals such as magnesium and lead, twice as abundant as cobalt and even more abundant than tin. Cerium can exist in two valence states, +3 [cerous, Ce(III)] and +4 [ceric, Ce(IV)] each possessing distinctly different chemistry and application possibilities.

The preparation of organic derivatives of $Ce^{+4}$ is difficult because of the tendency to oxidize components of the reaction system which reduces cerium to $Ce^{+3}$ as described in our U.S. Pat. No. 4,492,655 issued Jan. 8, 1985. Cerium (IV) alkoxides however are stable. They were first prepared by Bradley et al (J.Chem.Soc. 1956, 2260) from a process requiring the difficult preparation of ceric hexachlorodipyridinium complex. More recently a process using ceric ammonium nitrate (CAN) has been described in U.S. Pat. No. 4,489,000, issued Dec. 18, 1984.

One objective of this invention is to provide new derivatives of cerium. More particularly, one of the objectives of this invention is to prepare organo-cerium compounds in which cerium exhibits a valence of +4.

Another objective of this invention is to provide a method for preparing derivatives of cerium compounds in which the organic moiety contains an amino group.

Still a further objective of this invention is to provide a large class of novel cerium (IV) compounds which have properties suitable for use in several applications.

The new derivatives can be described as ceric alkanolatoamines. A search of the literature has failed to reveal an example of such cerium (IV) derivatives. Chloro(aminoalcoholato)- and nitrato(amino alcoholato)compounds of $Ce^{+3}$ and other trivalent lanthanides have been described in Russian Journal of Inorganic Chemistry 14 (3) 1969. These cerous compounds are described to be insoluble in methanol, acetone, ether and water and to have the following formula.

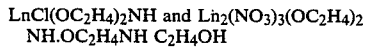

LnCl(OC$_2$H$_4$)$_2$NH and Ln$_2$(NO$_3$)$_3$(OC$_2$H$_4$)$_2$NH.OC$_2$H$_4$NH C$_2$H$_4$OH Reactions of metal alkoxides with alkanolamines are described in Metal Alkoxides by D. C. Bradley, R. C. Mehrotra and D. P. Gaur, Academic Press 1978, page 226-241.

In relation to the lanthanides there is the following:

"A comparative study of the reactivity of lanthanon isopropoxides viz, gadolinium, erbium, ytterbium, and yttrium isopropoxides towards ethanolamine indicated that only the hydroxyl group of ethanolamine was found to be replaceable with isopropoxy groups of these lanthanons [175, 176] thus resembling trivalent aluminum, gallium or iron analogs. The reactions with diethanolamine and triethanolamine also showed a similar behavior. All these derivatives are sparingly soluble or insoluble solids which decomposed on heating in vacuo. The bis-(diethoxyaminate) derivatives of all these elements lost one mole of diethanolamine to form bis-lanthanon tris-(diethoxyaminates) when heated under reduced pressure.

[Formulas omitted]

Summarizing the above work we note that the reactions of alkanolamines have been extended to alkoxides of boron, aluminum, gallium, silicon, germanium, tin, iron, vanadium, titanium, zirconium, niobium, tantalum, antimony, uranium, and lanthanons. Nevertheless, there is scope for much further work to elucidate structures of these interesting compounds."

The references cited above as 175 and 176 are Ph.D. theses, from the University of Rajasthan, Japipur, India (1970). In the Bradley et al. reference only Gd, Er, Yb, and Y isopropoxides are mentioned and compared to the trivalent aluminum, gallium or iron analogues.

THE INVENTION

The cerium derivative compounds of this invention can be named ceric alkanolatoamines, or amine alkoxides of cerium. The compounds of this invention are believed to have the following formula (formula I):

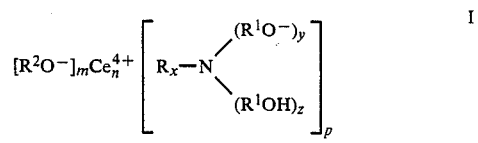

wherein n and p are each an integer of 1 or greater than one preferably between 1 and 20 and most preferably between 1 and 10; $R^1$ is an alkyl of 1 to 20 carbon atoms preferably 1 to 10 carbon atoms, most preferably 1 to 6 carbon atoms; R is a hydrogen or alkyl of 1 to 20 carbon atoms preferably 1 to 10 carbon atoms, most preferably 1 to 6 carbon atoms or a combination thereof; $R^2$ is an alkyl group of 1 to 20 carbon atoms preferably 1 to 10 carbon atoms, most preferably 1 to 6 carbon atoms; m is an integer from 0 to 3; x is an integer from 0 to 2; y is an integer from 1 to 3; z is an integer from 0 to 2, with the proviso that the sum of x, y and z is equal to 3, and $yp+m=4n$.

Where "n" is one, a monomeric compound exists. However, where the aminealkoxide moiety is difunctional, i.e., y is 2 or 3, a dimer or polymer can exist.

The product of the present invention is a ceric monomer, dimer or polymer where the ceric cation has a valence of +4. The cerium can be bonded or associated with either alkoxide groups present which include $[R^2O^-]_m$ and $[R^1O^-]_y$.

Under certain conditions, the ceric ion is more likely to react with the amine alkoxide group ($R^1O$) than with the alkoxide ($R^2O$). Under such circumstances one would not expect to have present ($R^1OH$), groups in the final product unless all alkoxide groups ($R^2O)_m$ had been displaced. Thus, in one embodiment of the present invention, in the foregoing formula, when z is greater or equal to 1, then m is zero and when m is greater or equal to one then z is zero.

It is believed that the amine group also participates in and/or contributes to the bonding of the ligands to the cerium. The foregoing empirical formula reflects the ionic relationship between the ceric cation and the alkoxide anion moieties present by requiring m+yp, the total number of alkoxides present, to equal 4n, "n" being the number of ceric cations present in the molecule.

The class of the ceric alkanolatoamines of the present invention can correspond to several structures as will be illustrated in greater detail below.

The compounds of this invention are derivatives and mixtures of derivatives of products prepared by reacting alkanolamines with ceric alkoxides. The alkanolamines useful in such syntheses have the following formula:

$$R_xN(R^1OH)_q \qquad (II)$$

wherein R is hydrogen, alkyl of 1 to 20 carbon atoms preferably 1 to 10 carbon atoms and most preferably from 1 to 6 carbon atoms, or a combination thereof; x is an integer from zero to two; q is an integer from 1 to 3 and the sum of x and q is equal to 3; $R^1$ is alkyl, straight or branched, having from 1 to 20 carbon atoms preferably 1 to 10 carbons and most preferably from 1 to 6 carbon atoms, and $(R^3O)_a$ where $R^3$ is alkyl from 1 to 3 carbon atoms and a is an integer from 1 to 12. Examples of R and $R^1$ substituents include methyl, ethyl, propyl, isopropyl, butyl, tertiary butyl, isobutyl, pentyl, isopentyl, hexyl, 2-ethyl hexyl, octyl, etc.

In preparing the ceric alkanolatoamines the ceric alkoxide starting material can be provided in a solution or dispersed in an inert solvent including ethers such as glymes and tetrahydrofuran, and benzene, etc. Ceric alkoxides that can be used as a starting material according to the present invention include those described in U.S. Pat. No. 4,489,000 issued Dec. 18, 1984, which is incorporated herein by reference. The ceric alkoxides include those derived from lower aliphatic alcohols such as methanol, ethanol, propanol, isopropanol, butanol, isobutanol, sec-butanol, tert-butanol, pentanol, isopentanol, sec-pentanol, and tert-pentanol. The ceric alkoxides also include those of higher aliphatic alcohols.

Most of the alkanolamine reagents are liquids themselves or are soluble in the same solvents identified above which are utilized with the ceric alkoxides. In general, the ceric alkoxides and alkanolamines react spontaneously at room temperature. Provided that one of the reactants, alkoxide or amine, is a liquid it is possible to carry out the reaction without a solvent. In general, the order or sequence of addition of the reactants is not significant in producing the compound of the present invention. It is contemplated, however, that under certain circumstances, e.g. poor mixing, if one reactant were added dropwise to the other, a different degree of branching or configuration could result in the final product as compared to the reverse addition of reactants.

A step of purification or isolation of the ceric alkanolatoamine reaction products from the reaction mixture is optional although the examples illustrate such purification steps. The final reaction mixture contains the desired product mixed with liberated alcohol and the inert solvents. The removal of the alcohol and solvents in most applications is unnecessary as they are not undersirable and can be tolerated.

We have found that compounds prepared with alkanolamines having formula (II) wherein "R" is hydrogen (a secondary amine) are less soluble in common solvents than compounds prepared with tertiary amines wherein "R" is not hydrogen.

The novel compounds of this invention are surprisinly more stable to hydrolysis and are easy to use in comparison with the starting ceric alkoxides. Their solubility in a variety of organic solvents makes them ready candidates for several important applications. For example, the compounds of this invention are suitable for use in such specialty areas as the production of ceramic powders, films, delayed action crosslinking agents, additives in plastics, silicones, paint and preparation of catalysts.

Many of the reactions between ceric alkoxides and alkanolamines are readily carried out at room temperature. Although it is contemplated that certain reactions may be desirably conducted at elevated temperature. Heating to accelerate reactions is generally not necessary if they readily occur at room temperature. Heating in such reactions may affect the structure of the reaction product and consequently the properties of the resulting products. For example, a reaction at elevated temperatures can tend to promote formation of dimers or polymers over monomers.

When an alkanolamine of formula (II) is used in which "q" is more than 1, there are more available sites in the alkanolamine for bonding with a cerium atom. For example, one possible product formed when two cerium atoms bond to two sites on each of two an alkanolamine molecules is a dimer. For example, in the following compound two alkanolamine molecules are bonded to two cerium atoms forming a dimer which is cyclic, having the following structure:

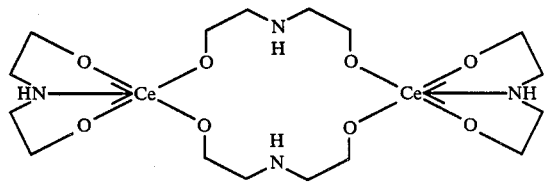

In the alternative, according to formula (I) two cerium atoms can bond to the two available sites in a single alkanolamine molecule to form a repetitive unit in a more or less linear or branched polymeric structure, as follows:

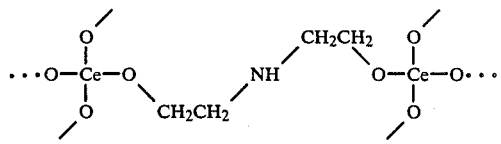

Depending upon the number of alkoxide groups displaced during the synthesis reaction, the resulting ceric compounds may form chelates, dimers or polymers. The extent to which chelation of these compounds takes place affects their solubility and reactivity. The product of such synthesis reactions may be mixtures of compounds of different structures since the reaction is heterogeneous.

Examples 1–15, below, illustrate compounds of the present invention that have been synthesized from reactions between ceric tetraalkoxides and various alkanolamines in different relative proportions. Examples 16–30 illustrate the syntheses of additional compounds within the present invention. These non-limiting examples serve merely to illustrate compounds and methods of making compounds of this invention.

EXAMPLE 1

Reaction of ceric tetra-isopropoxide with one equivalent of triethanolamine.

Triethanolamine (12.34 g., 0.0827 mole), freshly distilled. in 60 mls of dimethoxyethane solution was added to ceric isopropoxide solution (139.71 g. 0.0826 mole) at ambient temperature and the mixture was allowed to react for 25 minutes. A heavy yellow precipitate formed which totally dissolved in 1½ hours. The volatiles were distilled off under reduced pressure at 30° C., to give a dark yellow solid, 29.39 g. with a melting point (Mp) of 255° C., with decomposition starting at 100° C. Elemental analysis gave 40.05% cerium, 30.47% carbon, 4.95% hydrogen, 5.59% nitrogen. The solid is soluble in methanol, nitromethane, toluene, isopropyl alcohol, benzene, and water.

EXAMPLE 2

Reaction of ceric tetra-isopropoxide with two equivalents of triethanolamine.

Triethanolamine (25.16 g. 0.1686 mole), freshly distilled, in 60 mls of dimethoxyethane solution, was added to ceric isopropoxide solution (142.53 g. 0.0842 mole) at ambient temperature and the mixture was allowed to react for 1.8 hours. A heavy yellow precipitate formed and remained the next day. The volatiles were distilled off under reduced pressure at 30° C., to give a yellow solid, 38.50 g. having a melting point of 90° C., with decomposition. Titration of the solid showed 30.65% $Ce^{+4}$; elemental analysis gave 30.84% cerium, 33.91% carbon, 6.29% hydrogen, 7.11% nitrogen. The solid is soluble in methanol, nitromethane, toluene, isopropyl alcohol, benzene, and water.

EXAMPLE 3

Reaction of ceric tetra-isopropoxide with one equivalent of diethanolamine.

Diethanolamine (1.34 g. 0.0127 mole), freshly distilled, was added to ceric isopropoxide solution (21.55 g. 0.0127 mole). A light yellow solid precipitated. The solid dissolved overnight to give a clear orange solution. Workup as above yielded shiny, yellow-brown flakes, yield 4.65 g. There was partial melting and decomposition starting at 80° C. but solid still remained up until 250° C. Titration of the solid showed 36.60% $Ce^{4+}$; elemental analysis gave 43.21% cerium, 23.70% carbon, 4.81% hydrogen, 4.76% nitrogen.

Gas chromatogaphic analysis of the distillate confirmed, within experimental error, the theoretical displacement, i.e. that the diethanolamine had displaced 2 equivalents of isopropyl alcohol (IPA) per mole cerium.

EXAMPLE 4

Reaction of ceric tetra-isopropoxide with two equivalents of diethanolamine.

Diethanolamine (2.35 g., 0.0224 mole), freshly distilled, was added to ceric isopropoxide solution (18.93 g., 0.0112 mole) at room temperature. A light yellow slurry resulted. The volatiles were evaporated off to give a very dusty yellow powder, 4.20 g. The product did not melt, but decomposed gradually as it was heated to 175° C.

Titration of the solid showed 34.66% $Ce^{+4}$; elemental analysis gave 39.14% cerium, 27.00% carbon, 5.30% hydrogen, 8.01% nitrogen.

Gas chromatographic analysis of the distillate confirmed, within experimental error, the theoretical displacement; that diethanolamine had displaced 4 equivalents of IPA per mole cerium.

The product is soluble in dimethylformamide.

EXAMPLE 5

Reaction of ceric tetra-isopropoxide with one equivalent of ethanolamine.

Ethanolamine (0.83 g. 0.0136 mole, freshly distilled, was added neat to ceric isopropoxide solution (22.74 g. 0.0134 mole). A clear orange solution resulted. The volatiles were evaporated off to give a tan, glassy solid, 5.11 g. The melting point was 155° C. with decomposition. The solid dissolves in toluene, isopropanol and dimethylformamide.

Elemental analysis gave 40.63% cerium, 27.41% carbon, 5.78% hydrogen, 4.41% nitrogen.

Gas chromatographic analysis of the distillate confirmed, within experimental error, the theoretical displacement, i.e. that the ethanolamine had displaced 1 equivalent of IPA per mole cerium.

EXAMPLE 6

Reaction of ceric tetra-isopropoxide with two equivalents of ethanolamine.

Ethanolamine (1.56 g. 0.0255 mole), freshly distilled, was added neat to ceric isopropoxide solution (21.54 g. 0.0127 mole). A clear brown solution resulted. The volatiles were evaporated off to give a pale yellow solid, 4.92 g. The melting point was 250° C. with decomposition. The solid dissolves in isopropanol and n-butanol.

Elemental analysis gave 42.34% cerium, 21.62% carbon, 4.82% hydrogen, 8.61% nitrogen.

Gas chromatographic analysis of the distillate confirmed, within experimental error, the theoretical displacement, i.e. that the ethanlamine had displaced 2 equivalents of IPA per mole cerium.

EXAMPLE 7

Reaction of ceric tetra-isopropoxide with three equivalents of ethanolamine.

Ethanolamine (2.41 g. 0.0394 mole), freshly distilled, was added neat to ceric isopropoxide solution (22.07 g. 0.0130 mole). A clear brown solution resulted. The volatiles were evaporated off to give a pale yellow solid, 4.99 g. The product did not melt below 250° C. The solid dissolves in isopropanol and n-butanol.

Elemental analysis gave 48.71% ash (39.64% cerium), 22.09% carbon, 5.38% hydrogen, 10.70% nitrogen.

Gas chromatographic analysis of the distillate confirmed, within experimental error, the theoretical displacement, i.e. that the ethanolamine had displaced 3 equivalents of IPA per mole cerium.

EXAMPLE 8

Reaction of ceric tetra-isopropoxide with four equivalents of ethanolamine.

Ethanolamine (2.95 g., 0.0483 mole), freshly distilled, was added neat to ceric isopropoxide solution (20.36 g. 0.0120 mole). A clear brown solution resulted. The volatiles were evaporated off to give a pale yellow solid, 4.84 g. The product melted at 95° C. with decomposition. The solid dissolves in isopropanol and n-butanol.

Elemental analysis gave 41.68% cerium, 20.27% carbon, 5.01% hydrogen, 10.52% nitrogen.

Gas chromatographic analysis of the distillate confirmed, within experimental error, the theoretical displacement, i.e. that the ethanolamine had displaced 4 equivalents of IPA per mole cerium.

EXAMPLE 9

Reaction of ceric tetra-isopropoxide with one equivalent of N,N-diethyl-ethanolamine.

N,N-Diethyl-ethanolamine (1.77 g., 0.0151 mole), freshly distilled, was added neat to ceric isopropoxide solution (25.45 g. 0.0150 mole), giving a clear orange solution. Workup gave an extremely viscous red-orange residue, 6.58 g.

Elemental analysis gave 34.20% cerium, 31.96% carbon, 6.14% hydrogen, 4.08% nitrogen.

Gas chromatographic analysis of the distillate confirmed, within experimental error, the theoretical displacement, i.e. that the amine had displaced 1 equivalent of IPA per mole cerium.

The product is very soluble in toluene, hexane, isopropyl alcohol, diglyme, DMF, n-butyl alcohol and mixture of petroleum spirits.

EXAMPLE 10

Reaction of ceric tetra-isopropoxide with two equivalents of N,N-diethylethanolamine.

N,N-Diethylethanolamine (3.87 g., 0.0330 mole), freshly distilled, was added to ceric isopropoxide solution (27.77 g. 0.0164 mole), giving a clear orange solution. Workup gave an extremely viscous red-orange residue, 8.03 g.

Elemental analysis gave 31.53% cerium, 38.95% carbon, 7.93% hydrogen, 6.09% nitrogen.

Gas chromatographic analysis of the distillate confirmed, within experimental error, the theoretical displacement, i.e. that the diethylethanolamine had displaced 2 equivalents of IPA per mole cerium. The product had the same solubilities as in the 1:1 case, example 9.

EXAMPLE 11

Reaction of ceric tetra-isopropoxide with three equivalents of N,N-diethylethanolamine.

N,N-Diethylethanolamine (4.92 g. 0.0420 mole), freshly distilled, was added to ceric isopropoxide solution (23.59 g. 0.0139 mole), giving a clear orange solution. Workup gave a viscous red-orange residue, 7.63 g.

Titration of the solid showed 23.70% $Ce^{+4}$; elemental analysis gave 25.81% cerium, 43.79% carbon, 8.23% hydrogen, 7.78% nitrogen.

Gas chromatographic analysis of the distillate confirmed, within experimental error, the theoretical displacement, i.e. that the diethylethanolamine had displaced 3 equivalents of IPA per mole cerium.

The product has the same solubilities as the product in the 1:1 case, example 9.

EXAMPLE 12

Reaction of ceric tetra-isopropoxide with four equivalents of N,N-diethylethanolamine.

N,N-Diethylethanolamine (6.63 g. 0.0566 mole), freshly distilled, was added to ceric isopropoxide solution (23.83 g. 0.0014 mole), giving a clear orange solution. Workup gave a pourable red-orange fluid, 7.63 g.

Elemental analysis gave 30.72% ash (25.01% cerium), 42.13% carbon, 8.55% hydrogen, 8.06% nitrogen.

Gas chromatographic analysis of the distillate confirmed, within experimental error, the theoretical displacement, i.e. that the diethylethanolamine had displaced 4 equivalents of IPA per mole cerium.

This product has the same solubilities as that of the 1:1 case, example 9.

EXAMPLE 13

Reaction of ceric tetra-isopropoxide with one equivalent of N-ethyldiethanolamine.

N-Ethyldiethanolamine (2.25 g. 0.0169 mole, freshly distilled, was added to ceric isopropoxide solution (28.30 g. 0.0167 mole), giving a bright yellow precipitate. Evaporation of the volatiles gave a yellow solid, 6.63 g. having a melting point of 240° C. with decomposition.

Elemental analysis gave 39.29% cerium, 32.33% carbon, 5.92% hydrogen, 4.20% nitrogen.

Gas chromatographic analysis of the distillate confirmed, within experimental error, the theoretical displacement, i.e. that the ethyldiethanolamine had displaced 2 equivalents of IPA per mole cerium.

This product is soluble in toluene, IPA, DMF, n-butanol and petroleum distillates.

EXAMPLE 14

Reaction of ceric tetra-isopropoxide with two equivalents of N-ethyldiethanolamine.

N-Ethyldiethanolamine (3.49 g. 0.0262 mole), freshly distilled, was added to ceric isopropoxide solution (22.04 g. 0.0132 mole), giving a red-orange solution. Evaporation of the volatiles gave yellow-orange flakes, 5.96 g. having a melting point of about 80°–140° C. with decomposition.

Elemental analysis gave 33.88% cerium, 34.73% carbon, 6.26% hydrogen, 6.90% nitrogen.

Gas chromatographic analysis of the distillate confirmed, within experimental error, the theoretical displacement, i.e. showed that the ethyldiethanolamine had displaced 4 equivalents of IPA per mole cerium.

This product is soluble in toluene, hexane, IPA, diglyme, acetonitrile, DMF and n-butanol.

EXAMPLE 15

Reaction of ceric tetramethoxide with 4.2 equivalents of N,N-diethylethanolamine.

Ceric tetramethoxide (0.00690 mole) was slurried in 30 ml dimethoxyethane. A 10 ml solution of 0.0296 mole N,N-diethylethanolamine in DME was added. Within 10 minutes the bright yellow methoxide slurry changed to a deep orange, translucent solution. Work-up gave a product with the characteristics of the one obtained in example 12.

TABLE I

| Example | $R_xN(R^1OH)_m$ alkanolamine | | | | $Ce[OR^2]_4$ ceric alkoxide $R^2$ | Ratio of Ceric alkoxide to alkanol amine | Theoretical Displacement of IPA per mole Ce |
|---|---|---|---|---|---|---|---|
| | $R^1$ | R | m | x | | | |
| 16 | n-propyl | ethyl | 1 | 2 | isopropyl | 1:1 | 1 |
| 17 | n-butyl | ethyl | 1 | 2 | isopropyl | 1:2 | 2 |

TABLE I-continued

| Example | $R^1$ | R_xN(R^1OH)_m alkanolamine R | m | x | Ce[OR^2]_4 ceric alkoxide $R^2$ | Ratio of Ceric alkoxide to alkanol amine | Theoretical Displacement of IPA per mole Ce |
|---|---|---|---|---|---|---|---|
| 18 | isopentyl | ethyl | 1 | 2 | isopropyl | 1:2 | 2 |
| 19 | ethoxyethyl | ethyl | 1 | 2 | isopropyl | 1:1 | 1 |
| 20 | n-propyl | ethyl | 1 | 2 | isooctyl | 1:1 | 1 |
| 21 | n-butyl | H | 1 | 2 | isopropyl | 1:1 | 1 |
| 22 | n-hexyl | H | 1 | 2 | ethyl | 1:2 | 2 |
| 23 | n-propyl | propyl | 1 | 2 | ethyl | 1:1 | 1 |
| 24 | ethyl | ethyl | 2 | 1 | n-butyl | 1:2 | 4 |
| 25 | ethyl | butyl | 2 | 1 | ethyl | 1:2 | 4 |
| 26 | ethyl | pentyl | 1 | 2 | isopropyl | 1:1 | 1 |
| 27 | decyl | ethyl | 2 | 1 | isopropyl | 1:1 | 2 |
| 28 | propyl | n-hexyl | 2 | 1 | isopropyl | 1:1 | 2 |
| 29 | ethyl | ethyl | 1 | 2 | n-hexyl | 1:2 | 2 |
| 30 | ethyl | butyl | 1 | 2 | n-pentyl | 1:3 | 3 |

What is claimed is:

1. A compound having the formula:

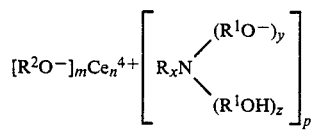

wherein R is one or more moieties selected from the group consisting of hydrogen and alkyl having from 1 to 20 carbon atoms, $R^2$ is an alkyl group having from 1 to 20 carbon atoms, $R^1$ is an alkyl group having from 1 to 20 carbon atoms, m is an integer from 0 to 3, y is an integer from 1 to 3, x and z are each an integer from 0 to 2, n and p are each an integer from 1 to 20, with the proviso that $m+yp=4n$, the sum of x, y and z is 3.

2. A compound of claim 1 wherein R is an alkyl group having from 1 to 10 carbon atoms.

3. A compound of claim 1 wherein R is an alkyl group having from 1 to 6 carbon atoms.

4. A compound of claim 1 wherein R is hydrogen.

5. A compound of claim 1 wherein $R^1$ is an alkyl group having from 1 to 10 carbon atoms.

6. A compound of claim 1 wherein $R^1$ is an alkyl group having from 1 to 6 carbon atoms.

7. A compound of claim 1 wherein $R^1$ is alkyl having from 1 to 3 carbon atoms.

8. A compound of claim 1 wherein $R^2$ is an alkyl group having from 1 to 10 carbon atoms.

9. A compound of claim 1 wherein $R^2$ is an alkyl group having from 1 to 6 carbon atoms.

10. A compound of claim 1 wherein $R^2$ is an alkyl having from 1 to 3 carbon atoms.

11. A compound of claim 1 wherein R, $R^1$, and $R^2$, may be the same or different, and are selected from alkyl having from 1 to 10 carbon atoms.

12. A compound of claim 1 wherein R, $R^1$, and $R^2$, which may be the same or different, are selected from alkyl having from 1 to 6 carbon atoms.

13. A compound of claim 1 wherein R, $R^1$, and $R^2$, which may be the same or different, are selected from alkyl having from 1 to 3 carbon atoms.

14. A compound of claim 1 wherein x is zero.

15. A compound of claim 1 wherein m is zero.

16. A compound of claim 1 wherein m is 1.

17. A compound of claim 1 wherein m is 2.

18. A compound of claim 1 wherein m is 3.

19. A compound of claim 1 wherein z is zero.

20. A compound of claim 1 which is a monomer wherein n is one.

21. A compound of claim 1 which is a dimer.

22. A compound of claim,1 which is a polymer.

23. A composition comprising the products resulting from a method comprising: reacting (i) an alkanolamine compound of the following formula:

$$R_xN (R^1OH)_q$$

wherein R is hydrogen or an alkyl of 1 to 20 carbon atoms, $R^1$ is an alkyl having 1 to 20 carbon atoms, x is an integer from 0 to 2, q is an integer from 1 to 3 and the sum of q and x is 3; with (ii) a ceric alkoxide compound of the following formula:

$$Ce(OR^2)_4$$

wherein $R^2$ is an alkyl having 1 to 20 carbon atoms.

24. The composition of claim 23, wherein said products comprise ceric alkanolatoamine products resulting from said method, an alkanolamine compound as defined in claim 23, and a ceric alkoxide compound as defined in claim 23.

25. A ceric alkoanolatoamine produced by a method comprising: reacting (i) an alkanolamine compound of the following formula:

$$R_xN (R^1OH)_q$$

wherein R is hydrogen or an alkyl of 1 to 20 carbon atoms, $R^1$ is an alkyl having 1 to 20 carbon atoms, x is an integer from 0 to 2, q is an integer from 1 to 3 and the sum of q and x is 3; with (ii) a ceric alkoxide compound of the following formula:

$$Ce(OR^2)_4$$

wherein Rphu 2 is an alkyl having 1 to 20 carbon atoms.

26. The ceric alkoanoloamine of claim 25, wherein R, $R^1$ and $R^2$, which may be the same or different.

27. The ceric alkanolatoamine of claim 26, wherein x is zero.

28. The ceric alkanolatoamine of claim 25, wherein $R^2$ is alkyl having from 1 to 6 carbon atoms.

* * * * *